United States Patent

Oishi et al.

Patent Number: 5,723,558
Date of Patent: Mar. 3, 1998

[54] FUMARIC ACID DERIVATIVE AND POLYMER THEREFROM

[75] Inventors: Tsutomu Oishi, Ube; Akio Hayashi, Kashiwa; Yoshihito Kadoma, Kobe, all of Japan

[73] Assignee: NOF Corporation, Tokyo, Japan

[21] Appl. No.: 817,629

[22] PCT Filed: Aug. 31, 1995

[86] PCT No.: PCT/JP95/01738

§ 371 Date: Mar. 27, 1997

§ 102(e) Date: Mar. 27, 1997

[87] PCT Pub. No.: WO97/08177

PCT Pub. Date: Mar. 6, 1997

[51] Int. Cl.$^6$ .................. C08F 130/02; C07C 69/60; C07F 9/10

[52] U.S. Cl. .................. 526/277; 560/222

[58] Field of Search .................. 526/277; 560/222

[56] References Cited

U.S. PATENT DOCUMENTS 4,707,306  11/1987  Leighton et al. .................. 260/501.12

*Primary Examiner*—Joseph L. Schofer
*Assistant Examiner*—Wu C. Cheng
*Attorney, Agent, or Firm*—Flynn, Thiel, Boutell & Tanis, P.C.

[57] ABSTRACT

A polymer obtained by polymerizing a fumaric acid derivative represented by the following general formula (1):

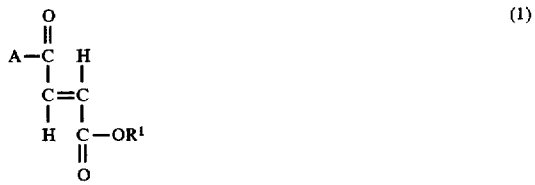

in which $R^1$ represents an alkyl group having 1–6 carbon atoms and A denotes a radical of

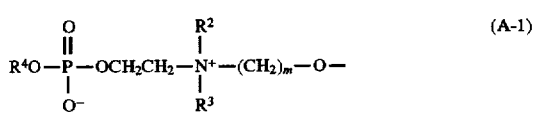

or

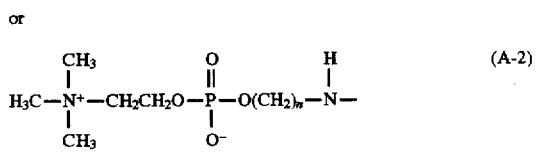

in which $R^2$ and $R^3$ represent each an alkyl group having 1–4 carbon atoms and may be identical with or different from each other. $R^4$ denotes an alkyl group having 1–6 carbon atoms or a benzyl group and m and n denote each an integer of 1–6.

4 Claims, 2 Drawing Sheets

▲ : Example 3-1

○ : Comparative Example 1

FUMARIC ACID DERIVATIVE AND POLYMER THEREFROM

FIELD OF THE TECHNIQUE

The present invention relates to a novel and useful fumaric acid derivative having a phospholipid-like molecular structure and to a polymer obtained therefrom, especially such a polymer that can be utilized as starting material for medical materials, biosensors, cosmetics and so on.

BACKGROUND OF THE TECHNIQUE

It has been made clear that the body of an organism contains various phospholipids which play each an important role for maintaining its life. For example, phospholipids have an intimate correlation with various metabolic processes in living organisms and, in addition, they play very important roles in the energy sources of brain tissues, in the transference and absorption of fat, in the coagulation of blood and in the dietetic sense of tastes for foods. Thus, phospholipids are components of cytoplasm, such as cell wall etc., and exhibit many functions in the life maintenance of totality of an organism.

On the other hand, many polymeric substances have found their use in the, field of medical materials and, for example, in the field of surgery, medical materials including artificial organs made of medical polymeric substances are in practical use. Artificial organs are substituted for or reconstruct lost biological functions, so that biological adaptability in organisms including, for example, anticarcinogenicity and anticorrosiveness, are required. When a biological material constituted of a polymeric substance without bioadaptability is used, problems may occur such as follows. Thus, when a medical material is brought into contact with, for example, blood etc., within a living body by a surgical operation, the surfaces of the medical material will soon become covered with a protein film and bring forth thereafter foreign body reactions on a cellular level with, for example, blood platelet, lymphocyte and macrophage, whereby a thrombus formation, an inflammation or a bulimia may occur. Therefore, a medical material requires a property for difficultly adhering proteins thereon, i.e., anti-protein-adhesion.

As a polymeric substance for medical material, polymer of methyl methacrylate is known. This polymethyl methacrylate is superior in the transparency and is used for a starting material of hard contact lens. Contact lenses made of polymethyl methacrylate are apt to suffer from adhesion of proteins, so that rinses of them should not be neglected. Also polymers of fumaric acid esters as well as of fumaramide are known for the polymeric substance of medical materials. While these polymers are superior in the transparency and in the permeability of gases such as oxygen gas etc., they are desired to be improved for their anti-protein-adhesion and bio-compatibility.

An object of the present invention is to provide a novel and useful fumaric acid derivative which can be polymerized easily and can produce by the polymerization a polymer which is superior in the anti-protein-adhesion, in the anti-thromboticity and in the bio-compatibility and has, in addition thereto, a high hardness, high transparency and high gas permeability.

Another object of the present invention is to provide a polymer of the above-mentioned fumaric acid derivative, which is superior in the anti-protein-adhesion, in the anti-thromboticity and in the biocompatibility and has, in addition thereto, a high hardness, high transparency and high gas permeability.

DISCLOSURE OF THE INVENTION

The fumaric acid derivative according to the present invention is a compound represented by the following general formula (1):

in which $R^1$ represents an alkyl group having 1–6 carbon atoms and A denotes a radical of

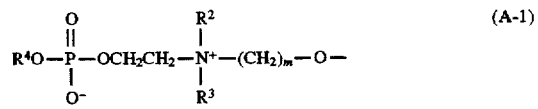

or

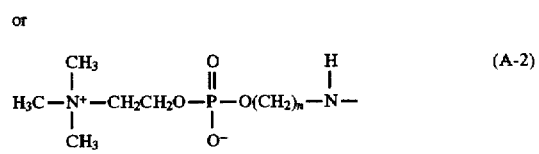

wherein $R^2$ and $R^3$ represent each an alkyl group having 1–4 carbon atoms and may be identical with or different from each other, $R^4$ denotes an alkyl group having 1–6 carbon atoms or a benzyl group and m and n denote each an integer of 1–6.

The polymer according to the present invention is a polymer of a fumaric acid derivative including the structural unit represented by the following general formula (2):

in which $R^1$ represents an alkyl group having 1–6 carbon atoms, A denotes a radical of

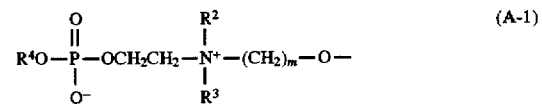

or

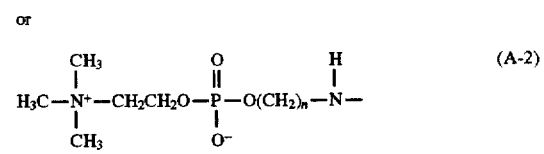

wherein $R^2$ and $R^3$ represent each an alkyl group having 1–4 carbon atoms and may be identical with or different from each other, $R^4$ denotes an alkyl group having 1–6 carbon atoms or a benzyl group and m and n denote each an integer of 1–6.

As the alkyl group having 1–6 carbon atoms represented by $R^1$ in the general formula (1), methyl, ethyl, n-propyl, isopropyl, n-butyl, isobutyl, sec-butyl, tert-butyl, n-pentyl, neopentyl, n-hexyl and the like may be enumerated.

The group denoted by A in the general formula (1) is a group having a structure similar to that of a polar group in a phospholipid and, thus, the fumaric acid derivative represented by the general formula (1) is represented, according to each specific type of the group A, either of the following general formula (1-1) or (1-2):

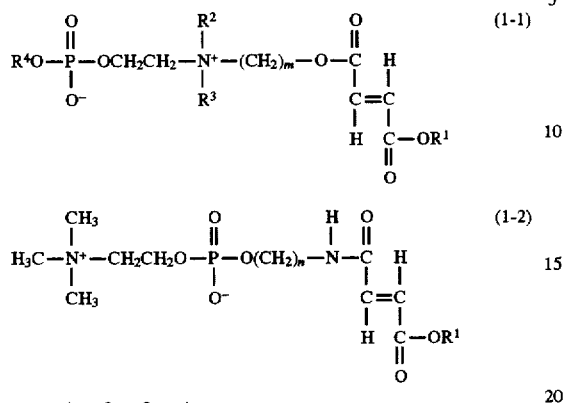

in which $R^1$, $R^2$, $R^3$, $R^4$ and m and n denote identical ones described above.

As the alkyl group having 1–4 carbon atoms represented by $R^2$ or $R^3$ in the general formula (1-1), methyl, ethyl, n-propyl, isopropyl, n-butyl, isobutyl, sec-butyl, tert-butyl and the like may be enumerated.

As the alkyl group having 1–6 carbon atoms represented by $R^4$ in the general formula (1-1), methyl, ethyl, n-propyl, isopropyl, n-butyl, isobutyl, sec-butyl, tert-butyl, n-pentyl, neopentyl, n-hexyl and the like may be enumerated.

As the concrete ones of the fumaric acid derivative represented by the general formula (1-1), for example, the followings may be enumerated:

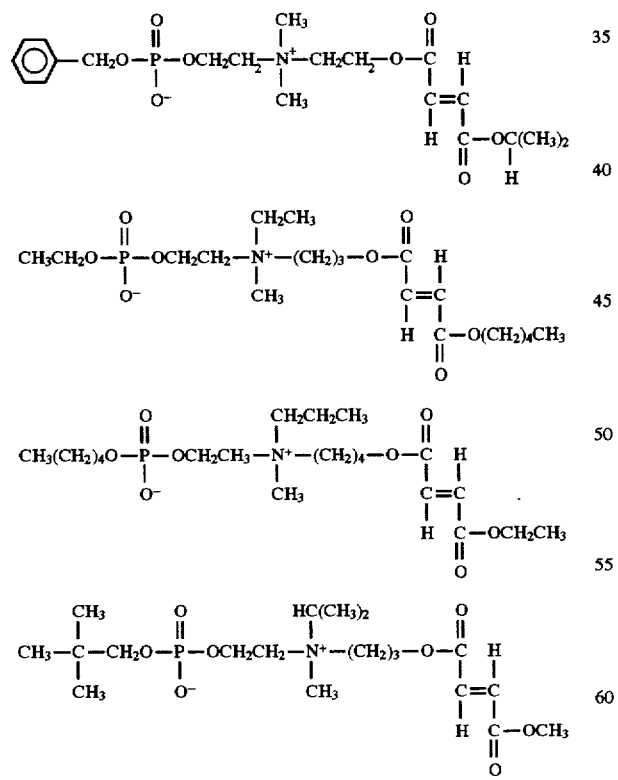

As the concrete ones of the fumaric acid derivative represented by the general formula (1-2), for example, the followings may be enumerated:

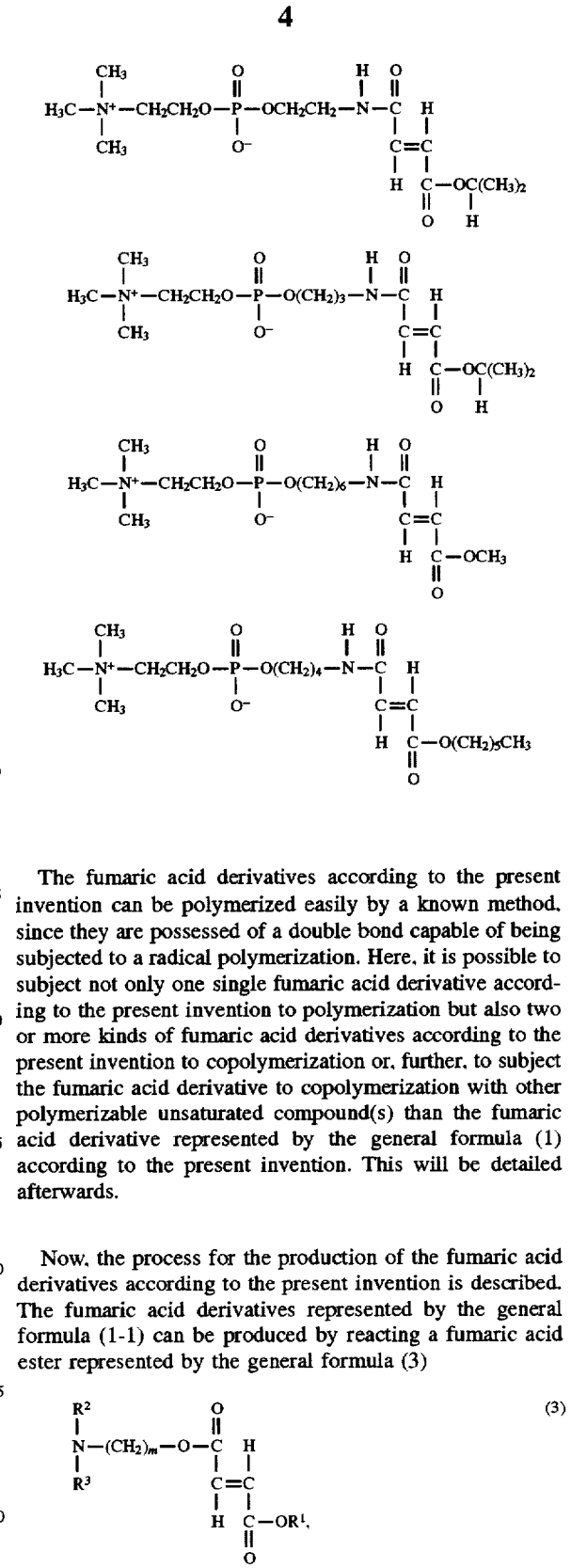

The fumaric acid derivatives according to the present invention can be polymerized easily by a known method, since they are possessed of a double bond capable of being subjected to a radical polymerization. Here, it is possible to subject not only one single fumaric acid derivative according to the present invention to polymerization but also two or more kinds of fumaric acid derivatives according to the present invention to copolymerization or, further, to subject the fumaric acid derivative to copolymerization with other polymerizable unsaturated compound(s) than the fumaric acid derivative represented by the general formula (1) according to the present invention. This will be detailed afterwards.

Now, the process for the production of the fumaric acid derivatives according to the present invention is described. The fumaric acid derivatives represented by the general formula (1-1) can be produced by reacting a fumaric acid ester represented by the general formula (3)

$$\begin{array}{c} R^2 \\ | \\ N-(CH_2)_m-O-C\phantom{xx}H \\ | \phantom{xxxxxxxxxxxx} | \\ R^3 \phantom{xxxxxxxxx} C=C \\ \phantom{xxxxxxxxxxx} | \phantom{x} | \\ \phantom{xxxxxxxxxx} H \phantom{x} C-OR^1, \\ \phantom{xxxxxxxxxxxxx} \| \\ \phantom{xxxxxxxxxxxxx} O \end{array} \quad (3)$$

in which $R^1$, $R^2$, $R_3$ and m denote those identical as above, with a phospholane compound represented by the general formula (4)

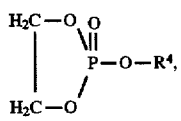

(4)

n which R⁴ denotes the identical one as above.

As concrete ones of the fumaric acid ester represented by the general formula (3), there may be enumerated, for example, N,N'-dimethylaminoethyl-isopropylfumarate, N-methyl-N'-ethylaminopropyl-isopropylfumarate, N-methyl-N'-n-butylaminohexyl-ethylfumarate, N,N'-dipropylaminohexyl-n-propylfumarate, N-methyl-N'-hexylaminoethyl-hexylfumarate, N-methyl-N'-isopropylaminoethyl-isopropylfumarate and N,N'-dimethylaminoethyl-tert-butylfumarate.

As concrete ones of the phospholane compound represented by the general formula (4), there may be enumerated, for example, 2-methoxy-2-oxo-1,3,2-dioxaphospholane, 2-ethoxy-2-oxo-1,3,2-dioxaphospholane, 2-propoxy-2-oxo-1,3,2-dioxaphospholane, 2-butyloxy-2-oxo-1,3,2-dioxaphospholane, 2-pentyloxy-2-oxo-1,3,2-dioxaphospholane and 2-hexyloxy-2-oxo-1,3,2-dioxaphospholane.

While the reaction of the fumaric acid ester represented by the general formula (3) with the phospholane compound represented by the general formula (4) can be effected without using any reaction medium, it is preferable to use a reaction medium. As concrete ones of the reaction medium, there may be enumerated organic solvents such as diethyl ether, tetrahydrofuran and chloroform. In the case of using a reaction medium, it is preferable to carry out the reaction by dropping a phospholane solution, prepared by dissolving the phospholane compound represented by the general formula (4) in the above-mentioned organic solvent, gradually under agitation into a fumaric acid ester solution, prepared by dissolving the fumaric acid ester represented by the general formula (3) in the above-mentioned organic solvent. Here, it is preferable to choose, as the organic solvent, one which does not or only scarcely dissolve the reaction product. The reaction is carried out preferably under a dry inert gas atmosphere.

While the reaction can proceed even at room temperature or below, the higher the temperature, the prompter is the reaction velocity. Since, however, side reactions will be facilitated at reaction temperatures above 50° C., the reaction is carried out desirably at a temperature of 50° C. or lower, preferably from room temperature to 40° C. The reaction duration may desirably be 24–50 hours, preferably 30–40 hours. The charge ratio of the fumaric acid ester represented by the general formula (3) to the phospholane compound represented by the general formula (4) may be 0.8:1–2:1, preferably 1:1–1.3:1, in a mole ratio of fumarate: phospholane.

After the reaction, the reaction product can be refined by dissolving it in an adequate solvent, such as chloroform, washing the resulting solution with water and introducing the organic solvent layer into a re-precipitating medium to cause reprecipitation. As the re-precipitating medium, diethyl ether, tetrahydrofuran and so on may be enumerated.

The reaction of the fumaric acid ester represented by the general formula (3) with the phospholane compound represented by the general formula (4) is shown by the following reaction scheme (5):

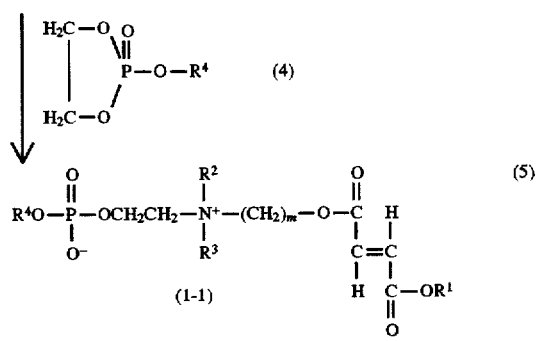

By the way, the fumaric acid ester represented by the general formula (3) can be prepared, for example, by a three step reaction course as shown in the following reaction scheme (6) using maleic anhydride and an alcohol (R¹OH) having an alkyl group R¹ as the starting materials. In the following reaction scheme, R¹, R², R³ and m denote the same ones as given above.

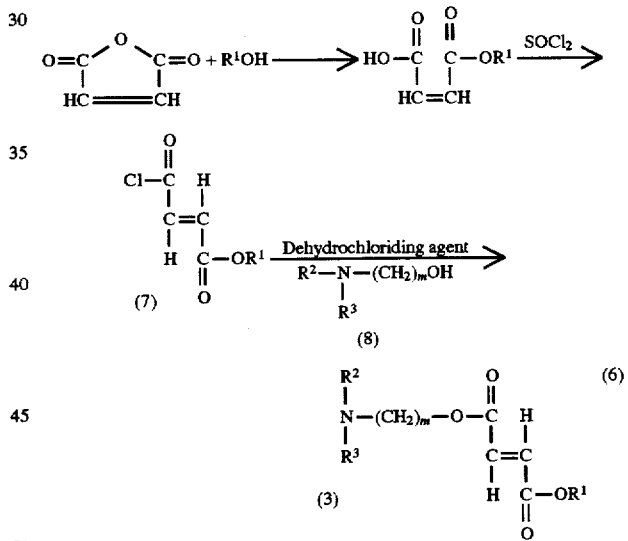

The first step reaction of the reaction scheme (6) can be realized by mixing maleic anhydride and the alcohol (R¹OH) and reacting at room temperature ~100° C. for 3–5 hours. Here, it is preferable to elevate the reaction temperature gradually in 3–4 steps.

In the second step reaction of the reaction scheme (6), the monoalkyl maleate obtained by the first step reaction is reacted with thionyl chloride to obtain the acyl chloride represented by the general formula (7). In this reaction, an isomerization from cis-form to trans-form proceeds together with the acyl chloride-forming reaction. The reaction may preferably be carried out in such a manner that a small amount of thionyl chloride is added to the monoalkyl maleate in a condition held at a temperature of 70°–90° C. to cause the reaction for 1–2 hours to accomplish the isomerization, whereupon the further reaction is caused for 2–4 hours while adding the remainder of thionyl choride gradually thereto at a temperature of 70°–90° C.

The reaction of the third step of the reaction scheme (6) can be realized by reacting the acyl chloride represented by the general formula (7) with the aminoalcohol represented by the general formula (8) at −40°~0° C. for 8~20 hours, preferably 10~12 hours in the presence of a dehydrochloriding agent. Here, it is preferable that a solution is prepared by dissolving the aminoalcohol and a dehydrochloriding agent in an adequate organic solvent and the so-obtained solution is cooled to the above-mentioned temperature, whereto a solution of the acid chloride in an appropriate organic solvent is added gradually. It is preferable to add the acyl chloride gradually, since the reaction is exothermal. As the dehydrochloriding agent, there may be enumerated trimethylamine, triethylamine, pyridine, urotropin, dimethylaminopyridine lutidine and so on. As the above-mentioned organic solvent, diethyl ether, tetrahydrofuran, dioxane and so on may be enumerated. After the reaction, the hydrochloride salt of the dehydrochloriding agent is filtered off, whereupon the refining can be effected by distillation under a reduced pressure.

As concrete ones of the aminoalcohol represented by the general formula (8), there may be exemplified 2-(N,N'-dimethylamino)ethanol, 3-(N,N'-dimethylamino)-1-propanol, 4-(N,N'-dimethylamino)-1-butanol, 5-(N,N'-dimethylamino)-1-pentanol, 6-(N,N'-dimethylamino)-1-hexanol, 2-(N,N'-diethylamino)ethanol, 3-(N,N'-diethylamino)-1-propanol, 4-(N,N'-dipropylamino)-1-butanol, 6-(N-ethyl-N'-methylamino)-1-hexanol, 2-(N-ethyl-N'-propyl-amino)ethanol.

The phospholane compound represented by the general formula (4) can be produced, for example, using phosphorus trichloride and ethylene glycol as the starting materials through a three-step reaction shown in the following reaction scheme (9). In the reaction scheme, $R^4$ denotes the same one as given above.

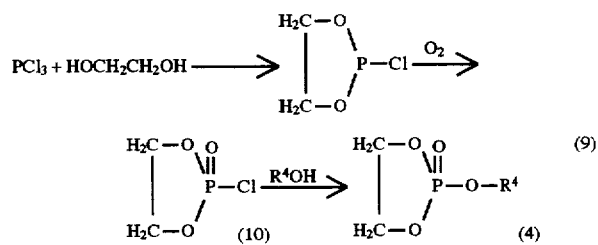

The first step reaction in the reaction scheme (9) can be realized by dissolving phosphorus trichloride in a reaction medium, such as methylene chloride, adding then ethylene glycol to the resulting solution dropwise gradually under agitation at a temperature near the room temperature so as to cause the reaction to proceed mildly and not to cause abrupt evolution of heat and hydrogen chloride gas and causing thereafter the reaction to further proceeded for 2~3 hours. Here, the reacting ratio of phosphorus trichloride and ethylene glycol may preferably be 1:0.8~1:5, preferably 1:1~1:3 in the mole ratio of phosphorus trichloride: ethylene glycol. By this reaction, 2-chloro-1,3,2-dioxaphospholane is obtained.

The second step reaction of the reaction scheme (9) can be realized by dissolving 2-chloro-1,3,2-dioxaphospholane obtained in the first step reaction in an organic solvent, such as benzene, and then bubbling through the resulting solution with oxygen or air at a temperature near the room temperature for 5~10 hours [J. Amer. Chem. Soc. 72, 5491 (1950); Chem. Ind. (London), 1962, 1828 (1962)]. By this reaction, 2-chloro-2-oxo-1,3,2-dioxaphospholane represented by the general formula (10) is obtained.

The third step reaction of the reaction scheme (9) can be realized by introducing 2-chloro-2-oxo-1,3,2-dioxaphospholane represented by the general formula (10) and the alcohol ($R^4OH$) containing an alkyl group represented by $R^4$ into a reaction medium, such as tetrahydrofuran etc., in a mole ratio of the formula (10) compound: $R^4OH$ of 1:0.8~1:5, preferably 1:1~1:3 and causing the reaction at −10°~0° C. for 1~3 hours. As concrete ones of the alcohol expressed by $R^4OH$, there may be enumerated methanol, ethanol, 1-propanol, 1-butanol,1-pentanol, 1-hexanol and benzyl alcohol.

Now, explanation is given for the process for the production of the fumaric acid derivative represented by the general formula (1–2). The fumaric acid derivative represented by the general formula (1–2) can be produced by reacting, in the presence of a tertiary amine, a fumaric acid ester represented by the general formula (11),

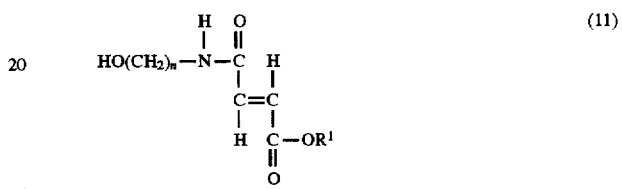

in which $R^1$ and n denote identical ones as given above, with a chlorophospholane compound, such as 2-chloro-2-oxo-1,3,2-dioxaphospholane represented by the general formula (10)

to obtain an alkyl-2-(2-oxo-1,3,2-dioxaphospholan-2-yloxy) alkylaminocarbonyl fumarate represented by the general formula (12),

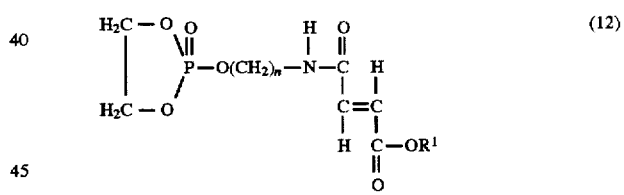

in which $R^1$ and n denoted the same ones as given previously, and reacting the so-obtained compound then with trimethylamine.

As concrete ones of the fumaric acid ester represented by the general formula (11), there may be enumerated, for example, isopropyl-(2-hydroxyethylaminocarbonyl) fumarate, ethyl-(2-hydroxybutylaminocarbonyl) fumarate, n-propyl-(2-hydroxyhexylaminocarbonyl) fumarate, n-hexyl-(2-hydroxyhexylaminocarbonyl) fumarate and tert-butyl-(2-hydroxyethylaminocarbonyl) fumarate.

The reaction of the fumaric acid ester represented by the general formula (11) with the chlorophospholane of, for example, the general formula (10) is carried out desirably at −30°~+50° C., preferably −20°~0° C. for 1~10 hours, preferably 4~8 hours. The charge ratio of both compounds may desirably be 0.8:1~2:1, preferably 1:1~1.3:1, in the mole ratio of the fumarate of formula (11): chlorophospholane of formula (10). As the tertiary amine employed here, trimethylamine, triethylamine, pyridine, urotropin, dimethylaminopyridine, lutidine and so on are enumerated. The amount of tertiary amine to be used may be 0.9~2 times, preferably 1~1.2 times mole of the chlorophospholane. While the reaction may be realized without using reaction medium, it is preferable to use an organic solvent, such as tetrahydrofuran.

The reaction of the compound represented by the general formula (12) with trimethylamine may preferably be carried out at −30°~+100° C., preferably room temperature ~60° C. for 5~100 hours, preferably 10~50 hours. The charge ratio of both compounds may preferably be 1:0.8~1:5, preferably 1:0.9~1:1.2, in a mole ratio of formula (12) compound: trimethylamine.

The reaction may preferably be carried out in a tightly sealed reactor so as not to cause trimethylamine to dissipate off. The reaction may preferably be effected under an inert gas atmosphere. While the reaction may be carried out without using reaction medium, it is preferable to use an organic solvent, such as acetonitrile.

After the reaction, the refining can be effected by recrystallization using an appropriate medium, such as acetonitrile.

The above reaction is shown by the following reaction scheme (13). In the scheme, $R^1$ and n denote the same ones as given above.

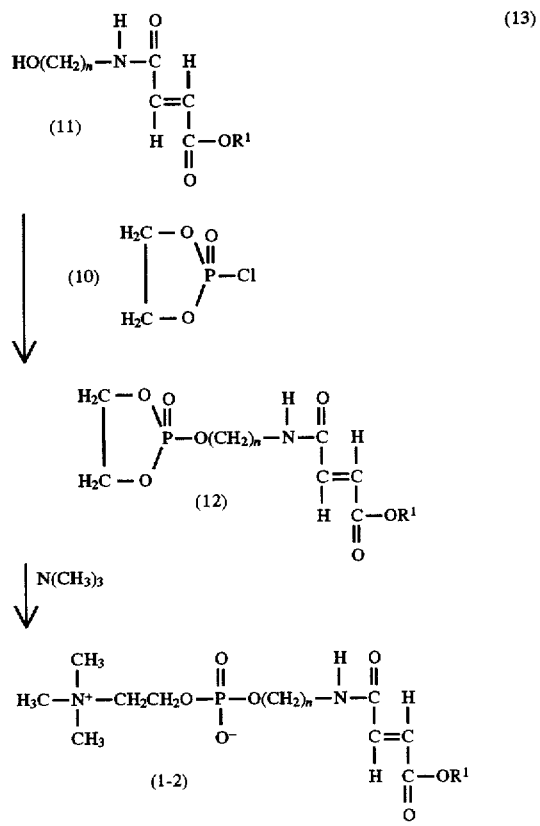

(in which n denotes the same one as given previously) in the presence of a dehydrochloriding agent at −40°~0° C. for 8~20 hours, preferably 10~12 hours. Here, it is preferable to prepare a solution by dissolving the aminoalcohol and the dehydrochloriding agent in an adequate organic solvent and cooling this solution to the temperature mentioned above, to which a solution of the acyl chloride in an adequate organic solvent is added gradually. The acyl chloride is added preferably in a gradual manner, since the reaction is exothermal. As the dehydrochloriding agent, trimethylamine, triethylamine, pyridine, urotropin, dimetylaminopyridine, lutidine and so on may be enumerated. As the organic solvent mentioned above, diethyl ether, tetrahydrofuran, dioxane and so on are enumerated. After the reaction, the hydrochloride salt of the dehydochloriding agent is filtered off, whereupon the refining can be effected by a reduced pressure distillation.

As concrete ones of the aminoalcohol represented by the general formula (14), there may be exemplified 2-aminoethanol, 3-aminopropanol, 4-aminobutanol, 5-aminopentanol and 6-aminohexanol.

The above reaction is shown by the following reaction scheme (15). In the scheme, n denotes the same one as given previously.

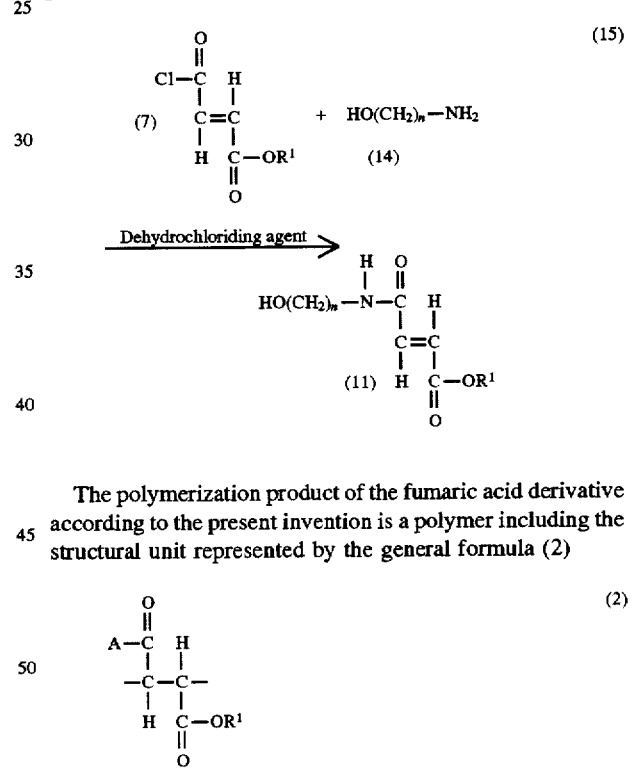

The polymerization product of the fumaric acid derivative according to the present invention is a polymer including the structural unit represented by the general formula (2)

in which $R^1$ and A denote the same ones given previously. In the polymer according to the present invention, other structural unit(s) than that represented by the general formula (2) may be included.

The group denoted by A in the general formula (2) is a group having a structure similar to that of a polar group in a phospholipid and, thus, according to each specific type of group A, the structural unit represented by the general formula (2) assumes either one structure of the following general formula (2-1) or (2—2).

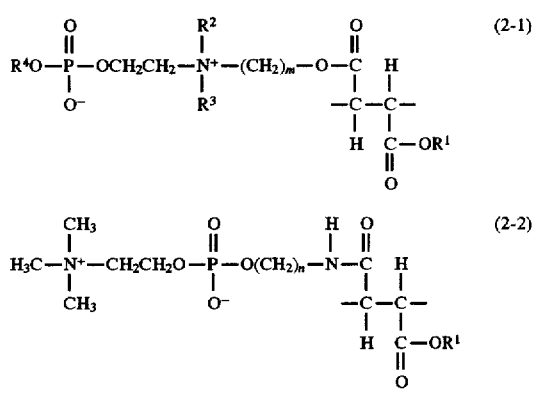

(In these formulae, $R^1$, $R^2$, $R^3$, $R^4$, m and n denote the same ones as given previously.)

The polymer according to the present invention is obtained by polymerizing the fumaric acid derivative represented by the general formula (1) in a known manner. Here, it is possible to polymerize the fumaric acid derivative represented by the general formula (1) solely for one single derivative or to copolymerize two or more derivatives or, further, to copolymerize it with other polymerizable unsaturated compound(s) than the fumaric acid derivative represented by the general formula (1).

As the above-mentioned other polymerizable unsaturated compound, there is no special limitation for the unsaturated compound, so long as it is copolymerizable with the fumaric acid derivative represented by the general formula (1). As concrete ones, for example, α-olefins, such as ethylene, propylene, isobutylene and the like; acrylic acid and esters thereof, such as acrylic acid, methyl acrylate, ethyl acrylate and the like; methacrylic acid and its esters, such as methacrylic acid, methyl methacrylate, ethyl methacrylate and the like; styrene and its derivatives, such as styrene, α-methylstyrene, nuclear substituted methylstyrenes, nuclear substituted chlorostyrene, divinylbenzene and so on; vinyl esters, such as vinyl acetate, vinyl propionate vinyl pivalate and so on; vinyl ethers, such as ethyl vinyl ether, n-butyl vinyl ether and the like; and others including vinyl compounds, such as vinyl chloride, vinylidene chloride, acrylonitrile, acrylamide and N-vinyl-pyrrolidone.

The structural unit represented by the general formula (2) existing in the polymer according to the present invention may preferably be, as a proportion occupying in the total structural units, 0.1~100 mole %, preferably 0.5~99 mole %, wherein the structural units derived from the other polymerizable unsaturated compound(s) may be 99.9 mole % or less, preferably 1~99.5 mole %.

The polymerization can be carried out easily in a known polymerization method, such as bulk polymerization, solution polymerization, suspension polymerization, emulsion polymerization or soap free emulsion polymerization. As the polymerization medium for carrying out a solution polymerization, for example, tetrahydrofuran, methanol, ethanol, water and mixtures of them may be employed.

It is preferable to use an initiator for the polymerization, for which there may be enumerated, for example, inorganic peroxides, such as potassium persulfate, ammonium persulfate and the like; organic peroxides, such as benzoyl peroxide, diisopropyl peroxy-dicarbonate, di-tert-butyl peroxide, tert-butyl peroxy-2-ethylhexanoate, tert-butyl peroxypivalate and tert-butyl peroxydiisobutyrate; and azo-compounds, such as 2,2'-azobisisobutyronitrile, 2,2'-azobis[2-(5-methyl-2-imidazolin-2-yl)propane] dihydrochloride, 2,2'-azobis-[2-(2-imidazolin-2-yl)propane] dihydrochloride, 2,2'-azobis[2-(4,5,6,7-tetrahydro-1H-1,3-diadipin-2-yl) propane] dihydrochloride and 2,2'-azobis[2-(3,4,5,6-tetrahydropyrimidin-2-yl)propane] dihydrochloride.

While the polymerization temperature may be different according to, for example, each specific kind of the initiator, it is usually preferable to choose a temperature from room temperature to 100° C., preferably from 50° to 80° C. The polymerization time may preferably be 5~100 hours, preferably 10~50 hours.

The polymers according to the present invention obtained as above are superior in the anti-protein-adhesion, in the antithrombotic property and in the bio-compatibility, since it has a phospholipid-like polar group derived from fumaric acid derivative and represented by the general formula (A-1) or (A-2) as given previously. They have moreover high hardnesses, high transparencies and high gas-permeabilities, stemmed from the structure of fumaric acid.

Consequently, the polymers according to the present invention can be used for the raw material for producing medical implements, such as contact lens, catheter, artificial organs and blood circuits, and for the raw material of surface coatings on these medical articles. Otherwise, they can be used for the raw material of sensors such as biosensors, and of cosmetics and others. The medical implements, such as contact lenses, catheter, artificial organs and blood circuit, made of, or coated with, the polymer according to the present invention are superior in the physiological functions, such as anti-protein-adhesion, antithromboticity and biocompatibility.

For obtaining molded articles such as the medical implements from the polymers according to the present invention, known methods can be employed, for example, a method comprising cutting a block of the polymer product obtained by, for example, bulk polymerization into a desired shape and polishing the so-shaped article. Formed articles can also be produced by a known molding technique, such as press molding etc.

For coating the surfaces of shaped articles such as medical implements with the polymer according to the present invention, for example, a technique may be employed in which the polymer according to the present invention is dissolved in an organic solvent to prepare a polymer solution and the surface of the shaped article is coated with the so-prepared solution, whereupon the organic solvent is removed.

As detailed above, the fumaric acid derivatives according to the present invention are novel and useful. The polymers of the fumaric acid derivatives according to the present invention are superior in the anti-protein-adhesion, anti-thrombotic property and biocompatibility, since they have the phospholipid-like polar group, -and, in addition they exhibit high hardness, high transparency and high gas-permeability.

THE BEST MODE FOR EMBODYING THE INVENTION

Figure 1:
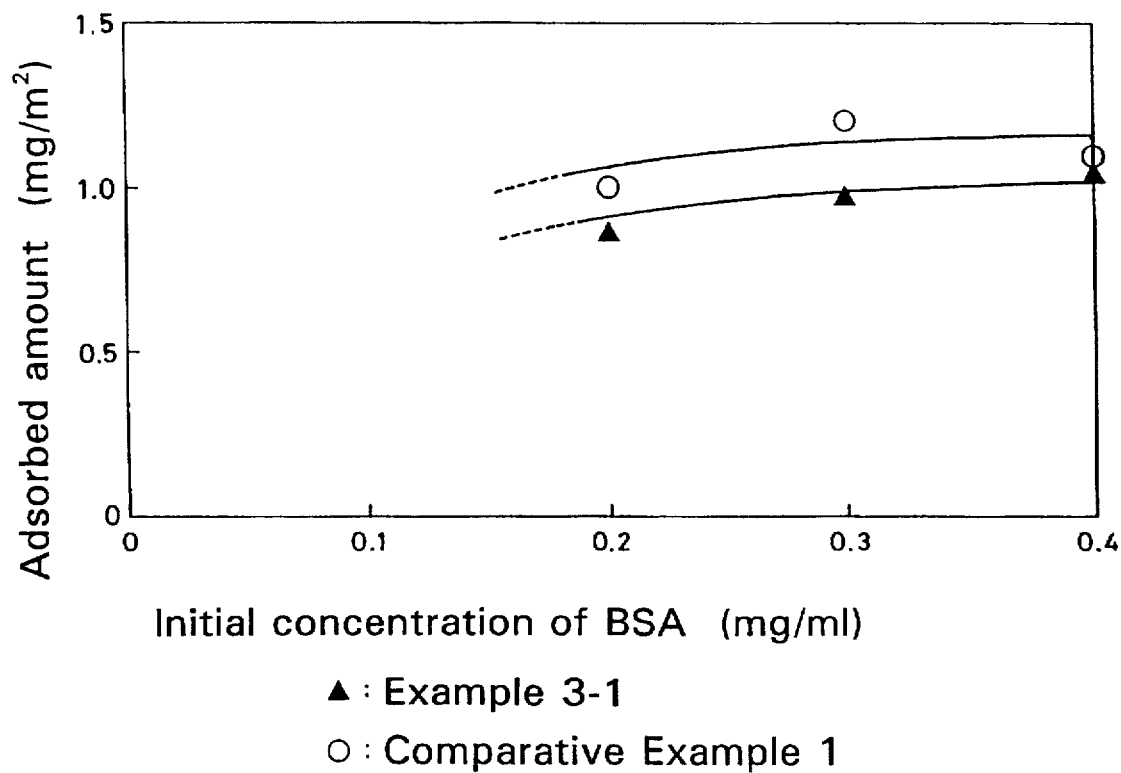
FIG. 1 is a graph showing the test results of Example 3-1 and Comparative Example 1.

Now, examples of the present invention are described.

Synthesis Example 1-1

1) Synthesis of Monoisopropyl Maleate 150 g (1.53 mol) of maleic anhydride and 96 g (1.60 mol) of isopropyl alcohol were mixed together at room temperature and agitated at 50° C. to reach complete dissolution, whereupon agitation was kept for 2 hours. Then, the temperature was elevated to 65° C. and the solution was agitated for 2 hours, followed by a temperature elevation to 80° C. and a further agitation for 2 hours. For ripening, the temperature was elevated to 90° C. and the solution was agitated for further 1 hour, whereby monoisopropyl maleate was obtained.

2) Synthesis of Isopropylfumaroyl Chloride

The temperature of the reaction product liquor for producing the monoisopropyl maleate obtained in 1) above was elevated to 80° C. and thereto were added stepwise 2.8 g (23.3 mmol) of thionyl chloride in four portions to cause isomerization to obtain monoisopropyl fumarate. This reaction was carried out so that the temperature of the reaction liquor did not exceed over 84° C.

To the so-obtained reaction liquor, 218.4 g (1.84 mol) of thionyl chloride were added dropwise at 80° C. over a period of 2 hours. Agitation was continued thereafter for 20 minutes while maintaining the temperature at 80° C. After the reaction was over, the unreacted thionyl chloride was distilled off under a reduced pressure, followed by a further distillation under an aspirator-reduced pressure to obtain 139.1 g (yield 51.4%) of isopropylfumaroyl chloride. The boiling point of the resulting isopropylfumaroyl chloride was found to be 85°–93° C./2.7 kPa.

3) Synthesis of Isopropyl-2-(dimethylamino)ethyl Fumarate 14.3 g (0.16 mol) of dimethylethanolamine and 16.2 g (0.16 mol) of triethylamine were dissolved in 250 ml of diethyl ether and the solution was cooled to −11° C. To this solution, 150 ml of a diethyl ether solution containing 28.3 g (0.16 mol) of isopropylfumaroyl chloride obtained in 2) above were added dropwise over a period of 3 hours with agitation. After the dropwise addition, the agitation was continued for 30 minutes, whereupon the mixture was agitated for further 10 hours at room temperature. After the reaction, hydrochloride salt of triethylamine was filtered off. The resulting concentrate of the reaction liquor was subjected to a distillation under a reduced pressure with an addition of a small amount of hydroquinone, whereby 14.6 g (yield 39.8%) of isopropyl-2-(dimethylamino)ethyl fumarate (in the following, abbreviated sometimes as IDAEF) represented by the following formula (16) were obtained. The boiling point of this IDAEF was found to be 92°–95° C./12 Pa.

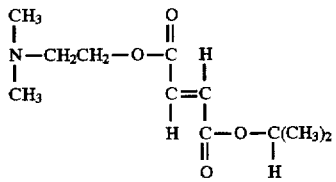
(16)

The analytical results of IDAEF are recited below:
$^1$H-NMR (δ (ppm), CDCl$_3$/TMS)
1.21 (d, 6H, —COOCH(CH$_3$)$_2$)
2.23 (s, 6H, —N(CH$_3$)$_2$
2.56 (tri, 2H, —COOCH$_2$ CH$_2$N(CH$_3$)$_2$)
4.23 (tri, 2H, —COOCH$_2$CH$_2$N(CH$_3$)$_2$)
5.05 (tetra, 1H, —COOCH(CH$_3$)$_2$)
6.80 (s, 2H, —OCOCH=CHCOO—)

Synthesis Example 1-2

1) Synthesis of 2-chloro-1,3,2-dioxaphospholane 200 g (1.46 mol) of phosphorus trichloride were dissolved in 300 ml of dichloromethane and, to this, 90.6 g (1.46 mol) of ethylene glycol were added dropwise at room temperature over a period of 10 hours with agitation. After the reaction was over, dichloromethane was distilled off under a reduced pressure, followed by distillation under an aspirator-reduced pressure to obtain 125.2 g (yield 69.1%) of 2-chloro-1,3,2-dioxaphospholane. The boiling point of this 2-chloro-1,3,2-dioxaphospholane was found to be 52°–54° C./2.7 kPa.

2) Synthesis of 2-chloro-2-oxo-1,3,2-dioxaphospholane 125.2 g (1.01 mol) of 2-chloro-1,3,2-dioxaphospholane obtained in 1) above were dissolved in 300 ml of benzene and oxygen was bubbled through this solution with agitation at room temperature for 17 hours to react with it. After distilling off benzene under an aspirator-reduced pressure, a reduced pressure distillation was effected to obtain 110.45 g (yield 76.8%) of 2-chloro-2-oxo-1,3,2-dioxaphospholane. The boiling point of this 2-chloro-2-oxo-1,3,2-dioxaphospholane was found to be 89°–92° C./0.1 kPa.

3) Synthesis of 2-benzyloyl-2-oxo-1,3,2-dioxaphospholane 3.0 g (0.028 mol) of benzyl alcohol and 2.8 g (0.028 mol) of triethylamine were dissolved in 100 ml of diethyl ether and the solution was cooled to −10° C. To this solution, a solution of 4.0 g (0.028 mol) of 2-chloro-2-oxo-1,3,2-dioxaphospholane obtained in 2) above in 80 ml of diethyl ether was added dropwise under a dry nitrogen atmosphere with agitation by mechanical stirrer over a period of 2 hours. After the dropping was over, the agitation was kept further 30 minutes. After the reaction was over, hydrochloride salt of triethylamine was filtered off. The filtrate obtained was used as such for the reaction in Examples below as the 2-benzyloyl-2-oxo-1,3,2-dioxaphospholane (in the following, abbreviated- occasionally as BODP) solution. It was confirmed by a $^1$H-NMR analysis of a colorless liquid obtained by concentrating a small aliquot part of the filtrate that BODP represented by the following formula (17) had been formed (yield 84.2%).

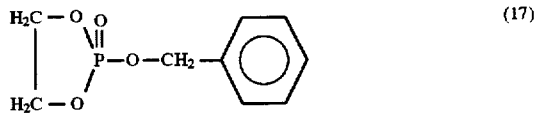
(17)

The analytical results of BODP are recited below:
$^1$H-NMR (δ (ppm), CDCl$_3$/TMS) 4.3–4.5 (m, 4H, —OCH$_2$CH$_2$O—) 5.16 (d, 2H, Ph—CH$_2$O—) 7.37 (s, 5H, Ph—)

EXAMPLE 1-1

9.0 g (0.039 mol) of IDAEF represented by the formula (16) obtained in Synthesis Example 1-1 were dissolved in 200 ml of diethyl ether. Separately from this, 0.03 mol of BODP represented by the formula (17) obtained in Synthesis Example 1-2 was dissolved in diethyl ether. The BODP solution was dropped into the IDAEF solution under a dry nitrogen atmosphere at 30° C. over a period of about 3 hours with agitation. After the dropping, agitation was effected at 30° C. for 36 hours to obtain isopropyl-2-[2-

(benzyloxyphosphoryl)-ethyldimethylammonio]ethyl fumarate (in the following, abbreviated occasionally as IBPF).

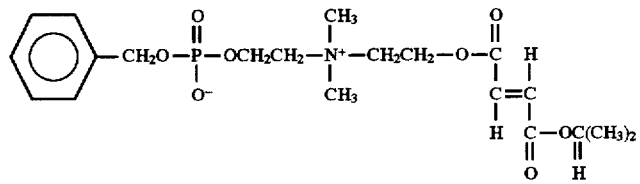

After the reaction was over, the viscous liquid deposited in the reaction liquor was separated from the reaction liquor by decantation. After the so-obtained deposited material was dissolved in chloroform, this solution was washed with a small amount of distilled water to remove the trace amount of hydrochloride salt of triethylamine. Then, anhydrous magnesium sulfate was added to the chloroform layer to dewater it, whereupon the solution was concentrated. Then, the resulting concentrate was dissolved in a small amount of tetrahydrofuran and reprecipitation in. diethyl ether was effected thereafter to purify IBPF, whereby 0.8 g (yield 6.0%) of an orange colored viscous liquid was obtained.

The analytical results of IBPF are recited below:

$^1$H-NMR ($\delta$ (ppm), CDCl$_3$/TMS) 1.21 (d, 6H, —COOCH(CH$_3$)$_2$ 2.72 (s, 6H, >N$^+$—(CH$_3$)$_2$ 3.20 (b, 2H, N$^+$—CH$_2$CH$_2$OCOCH=CH—) 3.65 (b, 2H, N$^+$—CH$_2$CH$_2$O—P) 3.92 (b, 2H, N$^+$—CH$_2$CH$_2$O—P) 4.52 (b, 2H, N$^+$—CH$_2$CH$_2$OCOCH=CH—) 4.92 (d, 2H, P—OCH$_2$—Ph) 5.06 (tetra, 1H, —COOCH(CH$_3$)$_2$) 6.80 (s, 2H, OCO—CH=CHCOO) 7.2–7.4 (m, 5H, —Ph)

Synthesis Example 1-3

8.2 g (0.13 mol) of monoethanolamine and 9.2 g (0.091 mol) of triethylamine were dissolved in 250 ml of tetrahydrofuran. Separately from this, 16.0 g (0.091 mol) of isopropylfumaroyl chloride obtained in 2) of Synthesis Example 1-1 were dissolved in 180 ml of tetrahydrofuran. After the above amine solution was cooled to −25° C., the above isopropylfumaroyl chloride solution was dropped into the amine solution over a period of 6 hours with agitation. After the dropping was over, the agitation was continued for further 30 hours while elevating the temperature gradually so as not to exceed −10° C. After the reaction was over, hydrochloride salt of triethylamine was filtered off and, then, the filtrate was concentrated, followed by a reduced pressure distillation to obtain 12.2 g (yield 66.7%) of isopropyl-2-(hydroxyethylaminocarbonyl) fumarate (in the following, abbreviated occasionally as IPHEF) represented by the formula (19) below in a yellowish viscous liquidous state. The boiling point of this IPHEF was found to be 175°~180° C./4.73 Pa.

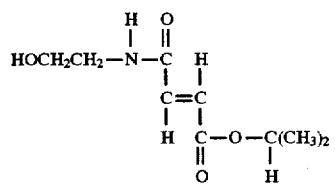

The analytical results of IPHEF are recited below:

$^1$H-NMR ($\delta$ (ppm), CDCl$_3$/TMS) 1.29 (d, 6H, —COOCH(CH$_3$)$_2$) 3.50 (tri, 2H, HOCH$_2$CH$_2$—NHCO—) 3.75 (tri, 2H, HOCH=CH$_2$—NHCO—) 4.4 (b, 1H, HOCH$_2$CH$_2$—NHCO—) 5.10 (tetra, 1H, —COOCH(CH$_3$)$_2$) 6.77, 6.82, 6.98, 7.05 (dd, 2H, —OCOCH=CHCOO—) 7.48 (b, 1H, HOCH$_2$CH$_2$—NHCO—)

EXAMPLE 1-2

9.6 g (0.048 mol) of IPHEF represented by the formula (19) obtained in Synthesis Example 1-3 and 6.7 ml (0.048 mol) of triethylamine were dissolved in 180 ml of tetrahydrofuran to obtain an IPHEF solution. Separately from this, 6.8 g (0.048 mol) of 2-chloro-2-oxo-1,3,2-dioxaphospholane obtained in 2) of Synthesis Example 1-2 were dissolved in 180 ml of tetrahydrofuran to obtain a solution of 2-chloro-2-oxo-1,3,2-dioxaphospholane. The above IPHEF solution was cooled to −15° C. and the above solution of 2-chloro-2-oxo-1,3,2-dioxaphospholane was dropped into the IPHEF solution over a period of 3.5 hours under a nitrogen atmosphere. Agitation was continued thereafter under the nitrogen atmosphere and the temperature was elevated gradually to room temperature over a period of 3 hours. After the reaction was over, deposited hydrochloride salt of triethylamine was filtered off under nitrogen atmosphere. The filtrate obtained was concentrated, whereby a crude product of isopropyl-2-(2-oxo-1,3,2-dioxaphospholan-2-yloxy)ethylaminocarbonyl fumarate (in the following, abbreviated occasionally as IPOPEF) was obtained.

This crude IPOPEF was dissolved in acetonitrile to prepare 150 ml of solution. This IPOPEF solution was charged in a pressure-resistant reactor tube and cooled to −40° C., whereupon 15.9 g (0.27 mol, about 5 times mole the theoretical amount for the IPHEF) of trimethylamine were added. Then, the pressure-resistant reactor tube was sealed under a nitrogen atmosphere, whereupon it was warmed to 40° C. using a water bath to effect the reaction while agitating by a stirrer for 24 hours. After the reaction was over, the reaction liquor was concentrated and, then, by a recrystallization from chloroform, 5.8 g (yield 33.5%) of isopropyl-2-(2-trimethylammoniumethylphosphoryl) ethylaminocarbonyl fumarate (in the following, abbreviated occasionally as IPTPAF) represented by the-following formula (20) were obtained as a white deliquescent powder.

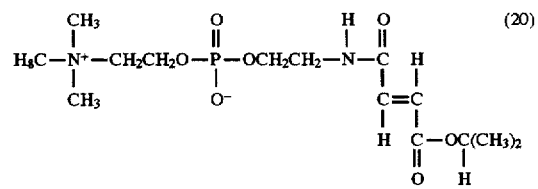

The analytical results of IPTPAF are recited below:

$^1$H-NMR ($\delta$ (ppm), CDCl$_3$/TMS) 1.21 (d, 6H, —COOCH(CH$_3$)$_2$) 3.12 (s, 9H, N$^+$—(CH$_3$)$_3$) 3.50 (b, 2H, N$^+$—CH$_2$CH$_2$O—P) 3.58 (b, 2H, —CONH—CH$_2$CH$_2$O—P) 3.92 (b, 2H, —CONH—CH$_2$CH$_2$O—P) 4.52 (b, 2H, N$^+$—CH, CH$_2$O—P) 5.06 (tetra, 1H, —COOH(CH$_3$)$_2$) 6.61, 6.70, 6.91, 7.00 (dd, 2H, —OCOCH=CHCOO—)

$^{13}$C-NMR ($\delta$ (ppm), CDCl$_3$/TMS) 22 (—COOCH(CH$_3$)$_2$) 42 (—N$^+$—(CH$_3$)$_3$) 55 (—CONH—CH$_2$CH$_2$O—P) 61

($N^+$—$CH_2CH_2O$—P) 65 ($N^+$—$CH_2CH_2O$—P) 67 (—COOCH($CH_3)_2$) 72 (—CONH—$CH_2CH_2O$—P) 132 (—NHCOCH=CH—COO—) 137 (—NHCOCH=CH—COO—) 167 (—NHCOCH=CH—COO—) 168 (—NHCOCH=CH—COO—)

EXAMPLE 2-1

A solution homo-polymerization of IBPF obtained in Example 1—1 was carried out in the manner as follows: 0.89 mmol of IBPF and 0.1 ml of tetrahydrofuran were charged in a polymerization tube. Then, 179 μ mol of tert-butyl peroxypivalate were added thereto as an initiator. This polymerization tube was placed in liquid nitrogen to freeze the solvent and a solid/liquid state change by degassing/thawing was repeated three times. Finally, dry nitrogen was introduced into the tube before it was sealed. The polymerization tube was held at 70° C. for 24 hours while shaking it to effect the polymerization of IBPF. Then, the polymerization was terminated by cooling the tube in ice water.

Then, the reaction liquor was introduced into a liquid mixture of diethyl ether: $CH_3Cl$=11:6 (in volume ratio) to cause the reaction product to precipitate to thereby wash it. This washing procedure was repeated two times. Finally, the supernatant liquid was removed by decantation to obtain a precipitate. This precipitate was washed by introducing it into a liquid mixture of diethyl ether: methanol=7:1 (in volume ratio). This washing procedure was repeated two times. The resulting precipitate was dried to obtain purified polymer. The polymerization conversion of this polymer was found to be 39.3% and the intrinsic viscosity [ηsp./C] thereof determined at 30° C. in 1/1 mixture of tetrahydrofuran/methanol was 0.04 dl/g.

The analytical results of the so-obtained polymer are recited below:

$^1$H-NMR (δ (ppm), $CDCl_3$/TMS) 1.0–1.2 (6H, ($CH_3$)$_2$CHOCO—CH—CH—COO—) 2.6–2.9 (6H, ($CH_3$)$_2$$N^+$<) 2.9–3.1 (2H, ($CH_3$)$_2$$N^+$—$CH_2CH_2$OCO—) 3.5–3.7 (4H, ($CH_3$)$_2$$N^+$—$CH_2CH_2$O—P—, ($CH_3$)$_2$ CHOCO—CH—CH—COO—) 3.8–4.1 (2H, ($CH_3$)$_2$$N^+$—$CH_2CH_2$O—P—) 4.0–4.2 (2H, ($C_3$)$_2$$N^+$—$CH_2CH_2$OCO—) 4.9 (2H, P—O—$CH_2$—Ph) 5.0 (1H, ($CH_3$)$_2$CHOCO—CH—CH—COO—) 7.1–7.4 (5H, P—$OCH_2$—Ph)

EXAMPLE 2-2

A solution copolymerization of IBPF obtained in Example 1-1 and styrene was carried out in the manner as follows: IBPF and styrene each in the amount given in Table 1 below were charged in a polymerization tube, whereto a 1/1 (volume ratio) liquid mixture of tetrahydrofuran/methanol was added as solvent. Then, an initiator solution (tert-butyl peroxypivalate) was added thereto. This polymerization tube was placed in liquid nitrogen to freeze the solvent and a solid/liquid state change by degassing/thawing was repeated three times. Finally, dry nitrogen was introduced into the tube before it was sealed. The polymerization tube was held at 70° C. for 24 hours while shaking it to effect the copolymerization. Then, the polymerization was terminated by cooling the tube in ice water.

Then, 1 ml of a liquid mixture of tetrahydrofuran:methanol=1:1 (volume ratio) was added to the reaction product to dissolve it. This solution was introduced into a liquid mixture of diethyl ether/methanol of 7/1 (volume ratio) to cause the reaction product to precipitate to thereby wash it. This washing procedure was repeated twice. Finally, the supernatant liquid was removed by decantation to obtain a precipitate. This precipitate was dried under vacuum to obtain purified copolymer. The polymerization conversion, intrinsic viscosity and proportion of the structural unit stemmed from IBPF in the so-obtained copolymer (which is denoted in the following occasionally as IBPF content) are given in Table 1. Here, the IBPF content was calculated from the result of $^1$H-NMR analysis.

TABLE 1

| Radical Copolymerization of IBPF and Styrene Reaction temp. = 70° C., in reaction medium of tetrahydrofuran/methanol of 0.05 ml/0.05 ml | | | | | |
|---|---|---|---|---|---|
| Run | 1 | 2 | 3 | 4 | 5 |
| Comonomer (a) | IBPF[2] | IBPF | IBPF | IBPF | IBPF |
| [1] (b) | ST[3] | ST | ST | ST | ST |
| Mole % of IBPF in Total Comonomers | 9.8 | 20.1 | 27.7 | 47.0 | 68.8 |
| Initiator (Amount in mg) | PBPV[4] (133) | PBPV (101) | PBPV (86.6) | PBPV (69.4) | PBPV (53.5) |
| Polimerization Time (hr) | 24 | 24 | 24 | 24 | 24 |
| Mole % of IBPF in Copolymer | 14.4 | 24.1 | 25.3 | 27.8 | 49.6 |
| Polymerization Conversion (%) | 13.3 | 42.1 | 47.6 | 66.0 | 53.4 |
| Intrins. Visc. [η$_{sp}$/C][5] (dl/g) | 0.10 | 0.13 | 0.10 | 0.14 | 0.07 |

Notes:
[1]: Comonomer (a) + comonomer (b) = 0.5 g
[2]: See the formula (18)
[3]: *ST = styrene
[4]: PBPV = tert-butyl peroxypivalate
[5]: Determined in 1/1 liquid mixture of tetrahydrofuran/methanol at 30° C.

EXAMPLE 2-3

The procedures of Example 2—2 were followed except that methylmethacrylate was used instead of styrene as the comonomer. The reaction conditions and the results are recited in Table 2.

TABLE 2

| Radical Copolymerization of IBPF and Methyl Methacrylate Reaction temp. = 70° C., in reaction medium of tetrahydrofuran/methanol of 0.05 ml/0.05 ml | | | | | |
|---|---|---|---|---|---|
| Run | 1 | 2 | 3 | 4 | 5 |
| Comonomer (a) | IBPF[2] | IBPF | IBPF | IBPF | IBPF |
| [1] (b) | MMA[3] | MMA | MMA | MMA | MMA |
| Mole % of IBPF in Total Comonomers | 9.9 | 19.8 | 29.7 | 49.6 | 68.7 |
| Initiator (Amount in mg) | PBPV[4] (130) | PBPV (103) | PBPV (87.1) | PBPV (68.1) | PBPV (52.3) |
| Polimerization Time (hr) | 24 | 25 | 24 | 24 | 24 |
| Mole % of IBPF in Copolymer | 6.1 | 12.8 | 22.1 | 34.1 | 63.4 |
| Polymerization Conversion (%) | 15.7 | 25.1 | 17.8 | 19.6 | 29.9 |
| Intrins. Visc. [η$_{sp}$/C][5] (dl/g) | 0.10 | 0.08 | 0.08 | 0.04 | 0.04 |

Notes:
[1]: Comonomer (a) + comonomer (b) = 0.5 g
[2]: See the formula (18)
[3]: MMA = Methyl methacrylate
[4]: PBPV = tert-butyl peroxypivalate
[5]: Determined in 1/1 liquid mixture of tetrahydrofuran/methanol at 30° C.

The analytical results of the copolymer of Run 1 of Table 2 are recited below:

$^1$H-NMR (δ (ppm), $CDCl_3$/TMS) 0.9–1.0 (3H, —$CH_2$C($CH_3$)COO$CH_3$) 1.0–1.2 (6H, ($CH_3$)$_2$CHOCO—CH—

CH—COO—) 1.5–2.0 (2H, —CH$_2$—C(CH$_3$)COOCH$_3$) 2.6–2.9 (6H, (CH$_3$)$_2$N$^+$<) 2.9–3.1 (2H, (CH$_3$)$_2$N$^+$—CH$_2$CH$_2$OCO—) 3.5–3.7 (7H, (CH$_3$)$_2$N$^+$—CH$_2$CH$_2$O—P—, (CH$_3$)$_2$CHOCO—CH—CH—COO—), —CH$_2$—C(CH$_3$)COOCH$_3$) 3.8–4.1 (2H, (CH$_3$)$_2$N$^+$—CH$_2$CH$_2$O—P—) 4.0–4.2 (2H, (CH$_3$)$_2$N$^+$—CH$_2$CH$_2$OCO—) 4.9 (2H, P—O—CH$_2$—Ph) 5.0 (1H, (CH$_3$)$_2$CHOCO—CH—CH—COO—) 7.1–7.4 (5H, P—OCH$_2$—Ph)

EXAMPLE 2-4

The procedures of Example 2-2 were followed except that n-butyl methacrylate was used instead of styrene as the comonomer. The reaction conditions and the results are recited in Table 3.

TABLE 3

Radical Copolymerization of IBPF and n-Butyl Methacrylate Reaction temp. = 70° C., in reaction medium of tetrahydrofuran/methanol of 0.05 ml/0.05 ml

| Run | 1 | 2 | 3 | 4 | 5 |
|---|---|---|---|---|---|
| Comonomer (a) | IBPF[2] | IBPF | IBPF | IBPF | IBPF |
| [1] (b) | BMA[3] | BMA | BMA | BMA | BMA |
| Mole % of IBPF in Total Comonomers | 10.1 | 20.0 | 29.5 | 49.8 | 70.0 |
| Initiator | PBPV[4] | PBPV | PBPV | PBPV | PBPV |
| (Amount in mg) | (103) | (86.4) | (75.0) | (61.6) | (53.2) |
| Polimerization Time (hr) | 24 | 24 | 24 | 24 | 24 |
| Mole % of IBPF in Copolymer | 10.9 | 17.2 | 28.1 | 44.8 | 56.9 |
| Polymerization Conversion (%) | 3.8 | 9.4 | 12.9 | 20.4 | 22.4 |
| Intrins. Visc. $|\eta_{sp}/C|$[5] (dl/g) | 0.10 | 0.06 | 0.05 | 0.04 | 0.04 |

Notes:
[1]: Comonomer (a) + comonomer (b) = 0.5 g
[2]: See the formula (18)
[3]: BMA = n-Butyl methacrylate
[4]: PBPV = tert-butyl peroxypivalate
[5]: Determined in 1/1 liquid mixture of tetrahydrofuran/methanol at 30° C.

EXAMPLE 2-5

A soap free radical emulsion co-polymerization of IBPF obtained in Example 1-1 with methyl methacrylate was carried out in the following manner: IBPF and methyl methacrylate were charged in a 200 ml four-neck flask each in the amount given in Table 4 below, whereto was added distilled water and the mixture was agitated at 70° C. by a mechanical stirrer at 450 revolutions per minute for about 1 hour under a dry nitrogen atmosphere. Then, an aqueous solution of potassium persulfate as an initiator was added thereto all at once to effect the copolymerization with agitation for 2 hours. Thereafter, the polymerization was terminated by immersing the flask in ice water to cool it.

Then, the reaction liquor was subjected to filtration with a glass filter (1G-3) to remove coarse particles and coagulated polymer. The so-obtained filtrate was subjected to a centrifugation at 4,000 revolutions per minutes for 30 minutes, whereupon the supernatant liquid was removed by decantation to obtain microspheres. The microspheres were re-dispersed in water and a centrifugation was carried out under the same condition. These procedures were repeated twice to remove the unreacted monomers and initiator. After the microspheres were further re-dispersed in methanol, centrifugation was effected twice under the same condition to remove the remaining methyl methacrylate. By a final drying, refined microspheres were obtained.

TABLE 4

| IBPF | 1.0 mmol |
|---|---|
| Methyl methacrylate | 100 mmol |
| Potassium persulfate | 0.75 mmol |
| Water | 100 ml |
| Agitation rate | 450 rpm |
| Temperature | 70° C. |
| Time | 2 hr |

EXAMPLE 2-6

A solution homo-polymerization of IPTPAF obtained in Example 1-2 was carried out in the following manner: 0.87 mmol of IPTPAF was charged in a polymerization tube and thereto was added 0.5 ml of distilled water to dissolve IPTPAF. Then, potassium persulfate was added thereto as the initiator in an amount of 9.99 mole % with respect to IPTPAF. This polymerization tube was placed in liquid nitrogen to freeze the solvent and, then, a solid/liquid phase change by degassing/thawing was repeated three times. Finally, dry nitrogen was introduced into the tube before it was sealed. The polymerization tube was held at 70° C. for 72 hours while shaking it to effect the polymerization of IPTPAF. Thereafter, the polymerization was terminated by cooling in ice water. Here, the reaction liquid was present as a homogeneous system.

Then, the distilled water was removed by distillation from the reaction liquid and the deposited materials were dissolved in methanol. After filtering off a small amount of insoluble matter (presumably the unreacted potassium persulfate), the filtrate was concentrated to about 1 ml. This concentrate was introduced into a 1/7 liquid mixture (volume ratio) of methanol/diethyl ether to cause the reaction product to precipitate to thereby wash it. This washing procedure was repeated twice. Finally, the supernatant liquid was removed by decantation to obtain a precipitated product. By drying this precipitated product, a refined polymer was obtained. The polymerization conversion of this polymer was found to be 39.2% and the intrinsic viscosity $[\eta_{sp}/C]$ thereof determined in a 1/1 liquid mixture of tetrahydrofuran/methanol at 30° C. was 0.041 dl/g.

EXAMPLE 2-7

A solution homo-polymerization of IPTPAF obtained in Example 1-2 was carried out in the following manner: 0.82 mmol of IPTPAF was charged in a polymerization tube and thereto was added 1.0 ml of dimethylformamide to dissolve IPTPAF. Then, di-tertbutyl peroxide was added thereto as the initiator in an amount of 23.7 mole % with respect to IPTPAF. This polymerization tube was placed in liquid nitrogen to freeze the solvent and, then, a solid/liquid phase change by degassing/thawing was repeated three times. Finally, dry nitrogen was introduced into the tube before it was sealed. The polymerization tube was held at 120° C. for 24 hours while shaking it to effect the polymerization of IPTPAF. Then, the polymerization was terminated by cooling in ice water. Here, the reaction liquid was present as a heterogeneous system.

Then, the supernatant liquid was removed from the reaction liquid by decantation and the reaction product was then dissolved in methanol. This solution was introduced into a 1/7 liquid mixture (volume ratio) of methanol/diethyl ether to cause the reaction product to precipitate to thereby wash it. This washing procedure was repeated twice. Finally, the supernatant liquid was removed by decantation to obtain a precipitated product. By drying this precipitated product, a refined polymer was obtained. The polymerization conversion of this polymer was found to be 37.0% and the intrinsic viscosity $[\eta_{sp}/C]$ thereof determined in a 1/1 liquid mixture of tetrahydrofuran/methanol at 30° C. was 0.037 dl/g.

EXAMPLE 2-8

A solution copolymerization of IPTPAF obtained in Example 1-2 and methyl methacrylate was carried out in the following manner: IPTPAF and methyl methacrylate were charged in a polymerization tube each in the amount as given in Table 5 below and thereto was added dimethylformamide as a solvent to dissolve the comonomers. Then, an initiator (tert-butylperoxy pivalate) was added thereto in an amount given in Table 5. This polymerization tube was placed in liquid nitrogen to freeze the solvent and, then, a solid/liquid phase change by degassing/thawing was repeated three times. Finally, dry nitrogen was introduced into the tube before it was sealed. The polymerization tube was held at 120° C. for 2 hours while shaking it to effect the copolymerization. Then, the polymerization was terminated by cooling in ice water. Here, the reaction liquid was present as a heterogeneous system.

Then, the supernatant liquid was removed from the reaction liquid by decantation and the reaction product was then dissolved in 1 ml of methanol. This solution was introduced into a 1/7 liquid mixture (volume ratio) of methanol/diethyl ether to cause the reaction product to precipitate to thereby wash it. This washing procedure was repeated twice. Finally, the supernatant liquid was removed by decantation to obtain a precipitated product. By drying this precipitated product, a refined copolymer was obtained. The reaction conditions and the material properties of the copolymer are recited in Table 5.

TABLE 5

| Radical Copolymerization of IPTPAF and Methyl Methacrylate | | |
|---|---|---|
| Run | 1 | 2 |
| Comonomer (a) | IPTPAF[2] | IPTPAF |
| [1] (b) | MMA[3] | MMA |
| Mole % IPTPAF in Total Comonomers | 9.9 | 19.8 |
| Initiator | tBPO[4] | tBPO |
| (Amount in mg) | (1.15) | (0.97) |
| Polimerization Time (hr) | 24 | 24 |
| Mole % IPTPAF in Copolymer | 2.72 | 4.22 |
| Yield (%) | 64.0 | 64.9 |
| Intrins. Visc. $[\eta_{sp}/C]^{5)}$ (dl/g) | 0.064 | 0.053 |

Notes:
[1]: Comonomer (a) + comonomer (b) = 0.5 g
[2]: See the formula (20)
[3]: MMA = Methyl methacrylate
[4]: tBPO = tert-butyl peroxide
[5]: Determined in 1/1 liquid mixture of tetrahydrofuran/methanol at 30° C.

EXAMPLE 2-9

The procedures of Example 2-5 were followed except that 1.0 mmol of IPTPAF obtained in Example 1-2 was employed in the place of IBPF, whereby a refined microspheric product was obtained.

EXAMPLE 3-1

An adsorption experiment of bovine serum albumin (hereinafter abbreviated occasionally as BSA) onto the microspheres obtained in Example 2-5 was carried out in the following manner:

First, four kinds of aqueous BSA solutions of different concentrations (0.1, 0.2, 0.3 and 0.4 mg/ml) were prepared. A light absorbancy at 280 nm of each of these aq. BSA solutions was determined using Shimadzu UV-200A spectrophotometer (Trademark, made by Shimadzu Kogyo K.K.). A calibration curve showing the relationship between the concentration of BSA and the 280 nm absorbancy was prepared. For the determination of the light absorbancy, a quartz cell (1 cm) was used. By the way, light absorbancies in the wave range from 400 to 240 nm were observed and the wave length of 280 nm at which the detection sensitivity was at the highest was adopted.

Then, three 30 ml Erlenmeyer flasks were provided and each flask was charged with 0.1 g of the microspheres obtained in Example 2-5. Each of these flasks was then charged with each 20 ml of each of the three kinds of aq. BSA solutions of 0.2, 0.3 and 0.4 mg/ml each prepared using a distilled water of pH 6.6 and was sealed. Thereafter, agitation was effected at 25° C. for 2 hours in order to cause the microspheres to contact with BSA sufficiently. Then, a centrifugation was effected at 4,000 rpm for 30 minutes, whereupon the supernatant liquid was collected by decantation. This supernatant liquid was further subjected to a centrifugation at 13,000 rpm for 30 minutes to remove microspheres. A light absorbancy of this supernatant liquid was determined at 280 nm, from which the BSA concentration in the supernatant liquid was calculated using the calibration curve prepared previously.

From the difference between the BSA concentrations before and after the adsorption experiment, the amount of BSA adsorbed on the microspheres was determined. Thus, assuming the difference in the BSA concentration to be $\Delta C$ (mg/ml), the volume of the aq. BSA solution used to be V (ml), the amount of the microspheres used to be Wm (g) and the specific surface area of the microspheres to be Sm ($m^2$/g), the adsorbed amount is calculated by the equation:

$$\text{Adsorbed amount (mg/m}^2\text{)} = (\Delta C \times V)/(Wm \times Sm)$$

The curve of adsorption isotherm obtained in this manner is given in FIG. 1.

EXAMPLE 3-2

Figure 2:
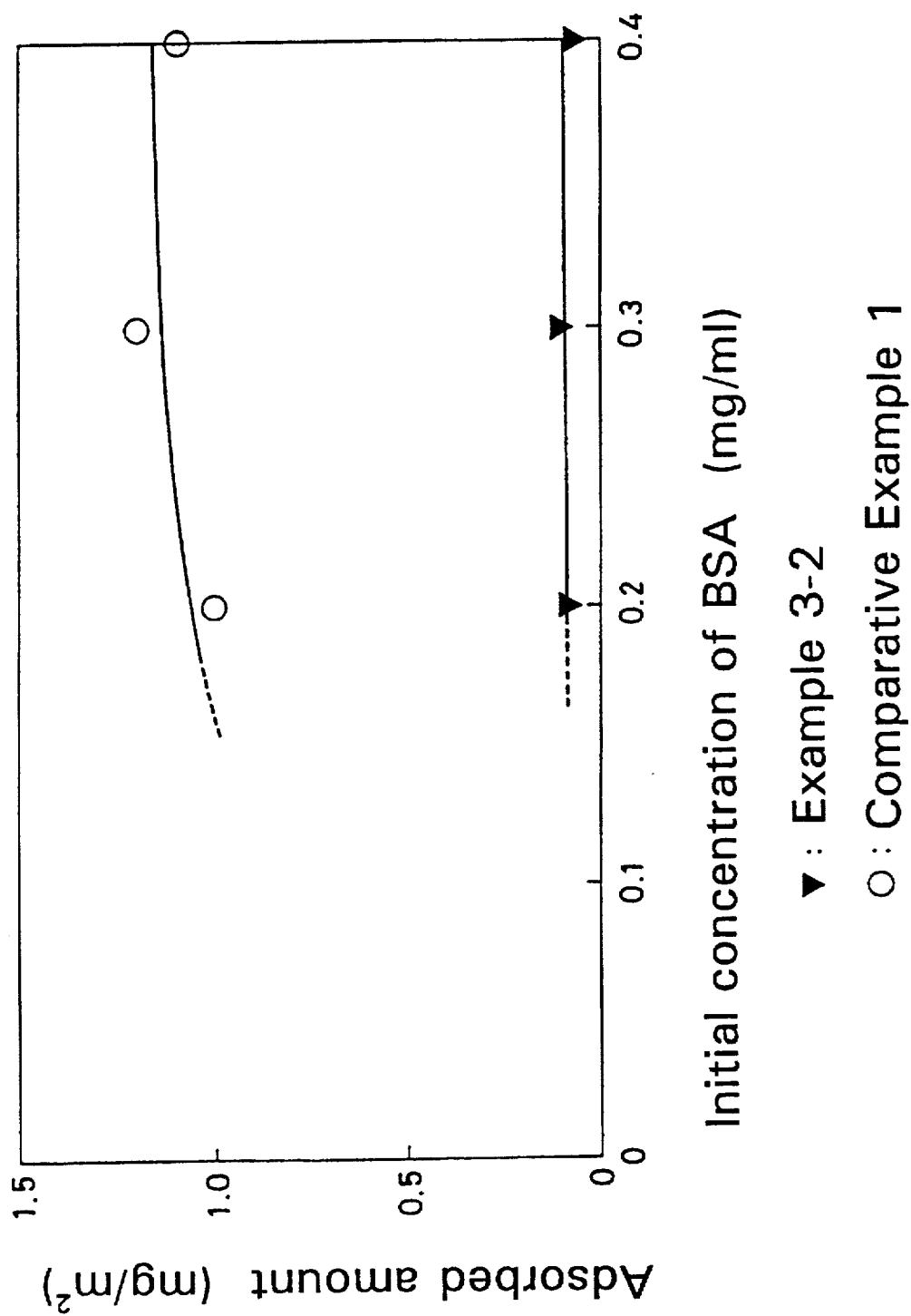
FIG. 2 is a graph showing the test results of Example 3-2 and Comparative Example 1.

An adsorption experiment of BSA onto the microspheres obtained in Example 2-9 was carried out in the same manner as in Example 3-1. The results are shown in FIG. 2.

Comparative Example 1

Under the conditions given in Table 6 below, microspheres made of a homopolymer of methyl methacrylate were obtained in the same manner as in Example 2-5. Using these microspheres, an adsorption experiment of BSA was carried out in the same manner as in Example 3-1. The results are shown in FIGS. 1 and 2.

TABLE 6

| Methyl methacrylate | 70 mmol |
|---|---|
| Potassium persulfate | 0.53 mmol |
| Water | 70 ml |

TABLE 6-continued

| Agitation rate | 350 rpm |
|---|---|
| Temperature | 70° C. |
| Time | 100 min. |

From the results shown in FIGS. 1 and 2, it is seen that the amount of BSA adsorbed on the microspheres in Example 2–5 and 2–9 is lower than that of Comparative Example 1. Therefore, it is clear that the polymers of fumaric acid derivatives according to the present invention are superior in the anti-protein-adsorption and that medical implements made of such polymers are excellent in the anti-thrombotic property.

POSSIBILITIES OF APPLICATION IN INDUSTRY

The fumaric acid derivatives according to the present invention are novel compounds and can easily be subjected to homo- or co-polymerization solely in itself or with other comonomer(s). Such a homo- or co-polymer of the fumaric acid derivative is possessed of a phospholipid-like polar group, so that it is superior in the anti-protein-adsorptivity, in the anti-thrombotic property and in the bio-compatibility. It has also a high hardness, high transparency and high gas-permeability, so that it can be utilized for the raw material of medical implements, biosensors, cosmetics and so on.

We claim:

1. A fumaric acid derivative represented by the following general formula (1)

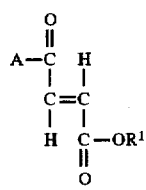

in which $R^1$ represents an alkyl group having 1–6 carbon atoms and A denotes a radical of

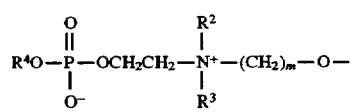

or

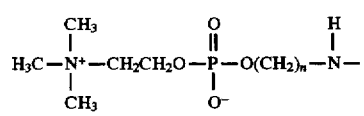

wherein $R^2$ and $R^3$ represent each an alkyl group having 1–4 carbon atoms and may be identical with or different from each other, $R^4$ denotes an alkyl group having 1–6 carbon atoms or a benzyl group and m and n denote each an integer of 1–6.

2. A fumaric acid derivative according to claim 1, which is represented by the following general formula (1-1):

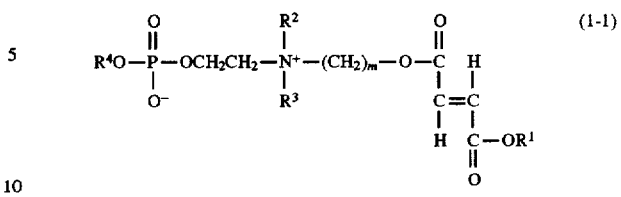

in which $R^1$ represents an alkyl group having 1–6 carbon atoms, $R^2$ and $R^3$ denote each an alkyl group having 1–4 carbon atoms and may be identical with or different from each other, $R^4$ denotes an alkyl group having 1–6 carbon atoms or a benzyl group and m denotes an integer of 1–6.

3. A fumaric acid derivative according to claim 1, which is represented by the following general formula (1-2):

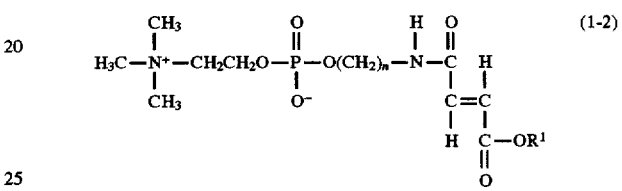

in which $R^1$ represents an alkyl group having 1–6 carbon atoms and n denotes an integer of 1–6.

4. A polymer comprising the structural unit represented by the following general formula (2)

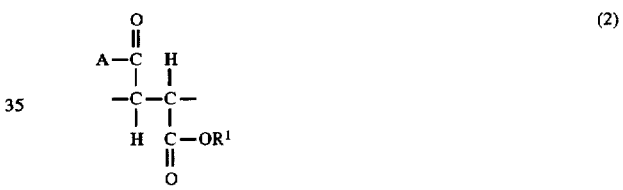

in which $R^1$ denotes an alkyl group having 1–6 carbon atoms and A represents either

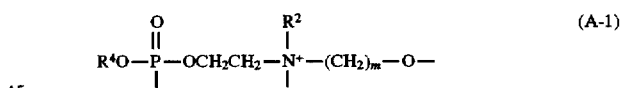

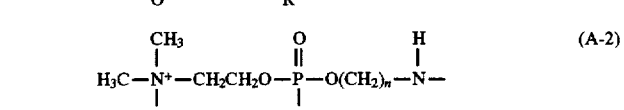

wherein $R^2$ and $R^3$ represent each an alkyl group having 1–4 carbon atoms and may be identical with or different from each other, $R^4$ denotes an alkyl group having 1–6 carbon atoms or a benzyl group and m and n denote each an integer of 1–6.

* * * * *